(12) United States Patent
Most, Jr.

(10) Patent No.: US 6,392,555 B1
(45) Date of Patent: May 21, 2002

(54) MEDICAL EQUIPMENT WARNING DEVICE

(76) Inventor: Clark Most, Jr., 1909 S. Badour Rd., Midland, MI (US) 48640

( * ) Notice: Subject to any disclaimer, the term of this patent is extended or adjusted under 35 U.S.C. 154(b) by 0 days.

(21) Appl. No.: 09/441,609

(22) Filed: Nov. 16, 1999

Related U.S. Application Data

(60) Provisional application No. 60/108,723, filed on Nov. 17, 1998.

(51) Int. Cl.⁷ ............................................... G08B 21/00
(52) U.S. Cl. .................. 340/664; 340/660; 128/204.23; 600/515; 600/529; 600/536
(58) Field of Search ................................ 340/664, 660; 73/861.44; 128/204.23, 204.21, 204.26, 204.18, 662.03, 663.01; 600/515, 536, 513, 529

(56) References Cited

U.S. PATENT DOCUMENTS

| | | | |
|---|---|---|---|
| 4,672,296 A | * 6/1987 | Griffin ............................ 322/1 |
| 5,051,673 A | * 9/1991 | Goodwin ..................... 318/481 |
| 5,128,552 A | * 7/1992 | Fang et al. .................... 307/66 |
| 5,239,995 A | 8/1993 | Estes et al. |
| 5,398,676 A | * 3/1995 | Press et al. ............. 128/204.23 |
| 5,485,850 A | * 1/1996 | Dietz .......................... 128/716 |
| RE35,295 E | 7/1996 | Estes et al. |
| 5,537,997 A | 7/1996 | Mechlenburg |
| 5,540,219 A | 7/1996 | Mechlenberg |
| 5,551,418 A | 9/1996 | Estes et al. |
| 5,598,838 A | * 2/1997 | Servidio et al. ........ 128/204.23 |
| 5,853,005 A | * 12/1998 | Scanion .................. 128/662.03 |
| 5,965,089 A | * 10/1999 | Jarvik et al. .................... 422/44 |

* cited by examiner

Primary Examiner—Edward Lefkowitz
Assistant Examiner—Davetta W. Goins
(74) Attorney, Agent, or Firm—Reising, Ethington, Barnes, Kisselle, Learman & McCulloch, P.C.

(57) ABSTRACT

The medical equipment warning device is employed in combination with a power operated medical treatment machine such as a sleep apnea treatment machine. The warning device includes a DC relay with contacts that are open when the relay is connected to an AC source. A signal generator is connected to a battery by the DC relay when the AC source is interrupted and contacts close the DC circuit. The signal generator produces an audible, visual or physical signal that warns a person that the AC power source has failed. Restoration of the AC power source activates the DC relay and opens the DC circuit thereby deactivating the signal generator.

8 Claims, 2 Drawing Sheets

MEDICAL EQUIPMENT WARNING DEVICE

The disclosure incorporates the medical equipment warning device disclosed in provisional patent application No. 60/108,723, filed on Nov. 17, 1998, whose priority is claimed for this application.

TECHNICAL FIELD

This invention relates to a medical equipment warning device and more particularly to a warning device that provides an audible warning if a medical device such as a sleep apnea treatment device fails or the devices power source fails.

BACKGROUND OF THE INVENTION

Sleep apnea is a transient cessation of respiration while a person is sleeping. The symptoms are varied and the cause of sleep apnea is unknown. Some individuals with sleep apnea may merely snore. Others reduce air intake and the oxygen level in their hemoglobin decreases. A reduction in hemoglobin oxygen level may be fatal if it is not corrected quickly.

Apnea is associated with restriction of the upper passages of the human respiratory system. The methodology for treating sleep apnea is to supply air to the respiratory system under pressure. The air under pressure tends to expand the air passages and thereby increase the flow of oxygen to the lungs. The air under pressure may be supplied by elaborate machines in a hospital for treatment of sleep apnea. The air under pressure may also be supplied to some individuals in their homes any time they sleep. The machines used in hospitals may supply air during inspiration at one pressure and during expiration at a lower pressure. These machines have central processing units that sense air flow rates, leakage, pressure, humidity and vibrations due to snoring. The measurements sensed may be recorded in the central processing unit. Some processing units make appropriate adjustments in air flow and pressure after each breath. The recorded measurements and the adjustments help doctors determine future treatment. These elaborate machines are relatively expensive. Individuals that require pressurized air when sleeping use less elaborate machines. Such machines are much less expensive. However, they are modified as required to meet the requirements of each individual with sleep apnea that requires such a machine. Some individuals for example, cannot tolerate pressurized air during expiration. Such individuals require a machine that supplies air at a lower pressure during expiration.

Hospitals generally have auxiliary power sources that supply electricity if the primary source fails for any reason. Auxiliary power systems provide electric power within seconds if there is an interruption in the primary system. Individual homes generally do not have auxiliary power sources and even if they do it takes at least a few minutes to disconnect the primary power source, connect the auxiliary power source and place the auxiliary power source in operation. A person that relies upon a medical device for assistance in the case of a life threatening disorder such as some forms of sleep apnea may not be able to wait for a repair crew to repair an electric power line, a transformer or a generator.

SUMMARY OF THE INVENTION

An object of the invention is to provide a warning device that produces a warning if the power to a medical device is interrupted.

Another object of the invention is to provide an audible warning when there is an interruption of power to a medical device.

A further object of the invention is to provide a warning device that produces a warning if the medical device has a malfunction.

A still further object of the invention is to provide a temporary power source that powers a medical device if the primary source is interrupted.

The medical equipment warning device has a relay that is deenergized when the primary power source is interrupted. Upon being deenergized, the relay connects an audio device to a storage battery and an audible signal is generated. The relay also connects the storage battery to the medical device to continue operation of the device.

At least one sensor senses an important operating parameter of the medical device. The sensor is preferably one that can determine if the medical device is not functioning properly. Upon detecting a malfunction, the sensor connects the storage battery to the audio device and an audible signal is generated.

DESCRIPTION OF THE DRAWINGS

The presently preferred embodiments of the invention are disclosed in the following description and in the accompanying drawings, wherein.

DESCRIPTION OF THE PREFERRED EMBODIMENTS

Figure 1:
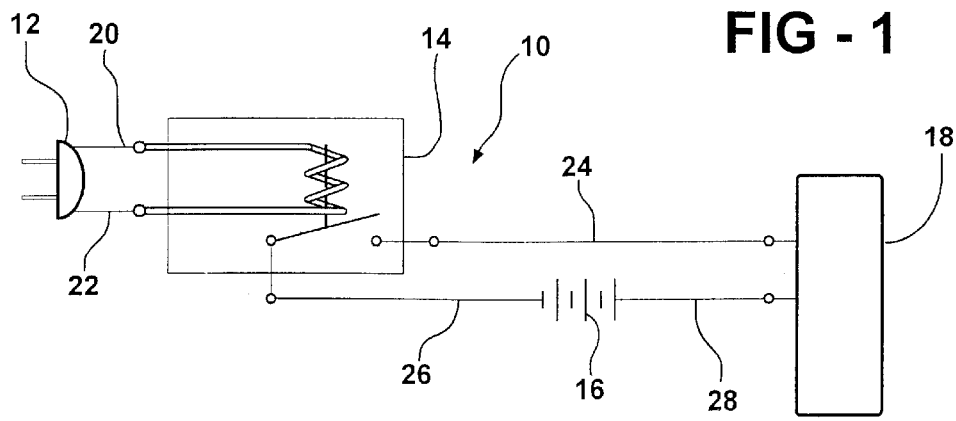
FIG. 1 is a circuit diagram of an alternating current interruption detector with an alarm signal generator.

The alternating current interruption detector 10, shown in FIG. 1, includes an AC power source 12, a relay 14, a battery 16 and a signal generator 18. The relay 14 is energized by a 120 volt alternating current and has contacts that are opened when the relay is connected to a 120 volt Ac source by lines 20 and 22. The signal generator 18 for individuals with the ability to hear is a sound generator. The sound generator 18 can be a bell or a buzzer but is preferably a solid state sound device. For individuals with impaired hearing, the signal generator 18 can be a flashing light, a vibrator or other device that will alert a person. Combinations of signal generators 18 can also be employed. One terminal on the relay 14 is connected to the sound generator 18 by a line 24. The battery 16 has one terminal connected to the relay 14 by a line 26 and another terminal connected to the sound generator 18 by a line 28. An interruption of current to the relay 14 from a power source 12 will allow the contacts in the relay to close and connect the battery 16 to the sound generator 18. The sound generator 18 will produce sound until the power source 12 resumes the supply of current to the relay 14 and opens the relay contact. The sound generator 18 will also stop producing sound if the battery 16 runs down or if the circuit connecting the battery to the sound generator 18 is opened by a switch provided for that purpose. The current interruption detector 10 can be used with or without a medical device.

Figure 2:
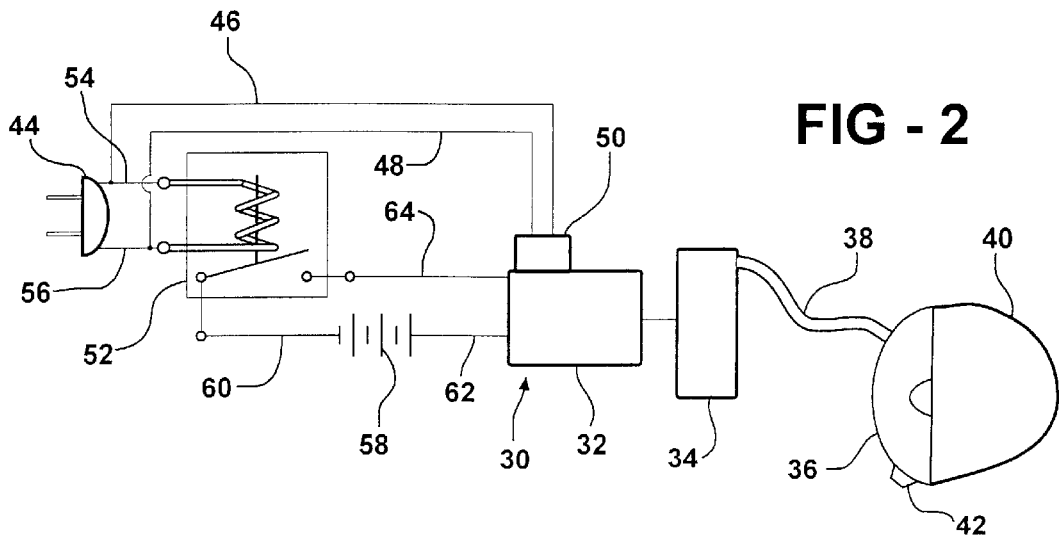
FIG. 2 is a circuit diagram of a continuous positive air pressure medical device control system with an auxiliary direct current power source.

The continuous positive air pressure medical device 30 shown in FIG. 2 is connected to an AC interruption detector and an auxiliary. direct current power source as shown in FIG. 2. The device 30 includes an electric motor 32 and a compressor or fan 34. The compressor 34 supplies air under pressure to a mask 36 through a supply tube 38. A band 40 holds the mask 36 over a person's nose. An air discharge 42 is attached to the mask 36 for discharging air from the lungs of a person wearing the mask during expiration.

The electric motor 32, as shown in FIG. 2, is a DC motor. The motor 32 is connected to an AC power source 44 by lines 46 and 48 through an AC to DC converter 50.

A relay 52 is connected to the AC power source 44 by lines 54 and 56. A battery 58 is connected to the relay 52 by a line 60 and to the electric motor 32 by a line 62. A line 64 connects the relay 52 to the motor 32. When the AC power source 44 is supplying current to the relay 52, contacts in the relay are held open. An interruption of current from the AC power source 44 will allow contacts in the relay 52 to close and connect the battery 58 to the motor 32. Upon the resumption of the supply of current from the AC power source 44 to the relay 52, the contacts in the relay are opened and the battery 58 is disconnected from the motor 32. With the control circuit of FIG. 2 the compressor 34 will automatically continue to supply compressed air to the mask 36 when there is an interruption in current from the AC power source 44.

Figure 3:
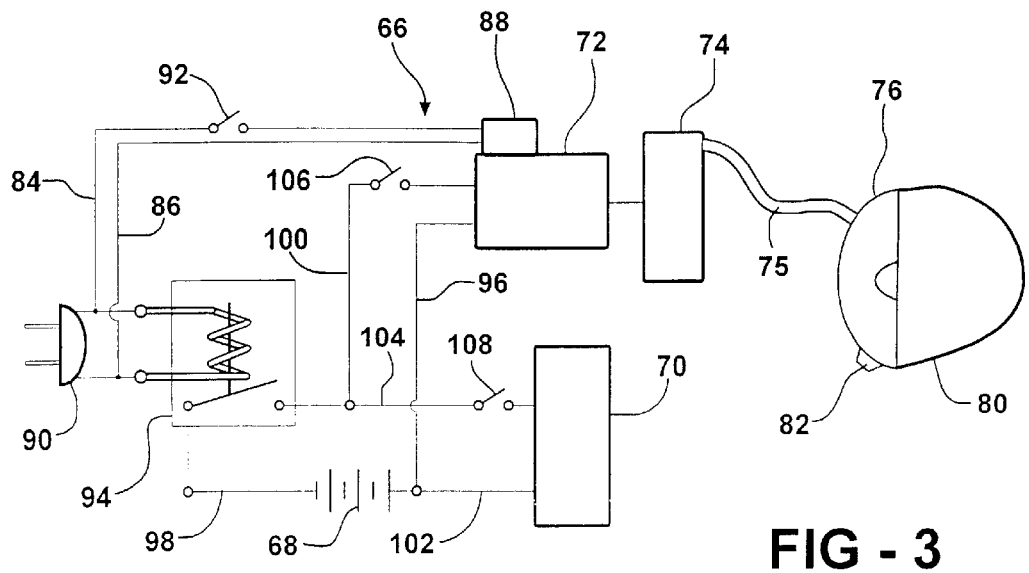
FIG. 3 is a circuit diagram of a continuous positive air pressure medical device control system with an alternating current interruption detector, an audible alarm and an auxiliary direct current power source.

A continuous positive air pressure sleep apnea treatment device 66 with an auxiliary power source battery 68 and an audible alarm 70 is shown in FIG. 3. The treatment device includes a DC motor 72 that drives a compressor 74. The compressor 74 supplies air under pressures through a supply tube 75 to a mask 76 that covers the nose of a person using the device. A strap 80 holds the mask 76 in place. An air discharge 82 permits the discharge of used air during expiration by the person wearing the mask 76.

The DC motor 72 is connected to an AC power source 90 by lines 84 and 86. An AC to DC converter 88 mounted on the motor 72 converts the AC voltage to a DC voltage to run the motor. A switch 92 is provided for turning the motor 72 off.

An interruption in power to the power source 90 will cause the normally open contacts in the relay 94 to close. When the relay 94 is closed, the battery 68 has one terminal connected to the motor 72 by a line 96 and another terminal connected to the motor by a line 98, the relay 94 and a line 100. A line 102 connects the battery 68 to the audible alarm 70 and to line 96, which runs to the motor 72. The circuit to the relay 94 is completed by line 104 to the alarm and by line 100 to the motor. An interruption in current from the AC power source 90 allows contacts in the relay 94 to close and connect the battery 68 to the alarm 70 and motor 72. A switch 106 is provided to turn off the motor 72 when it is connected to the battery 68. A switch 108 is provided to disable the audible alarm 70 when it is not required.

Figure 4:
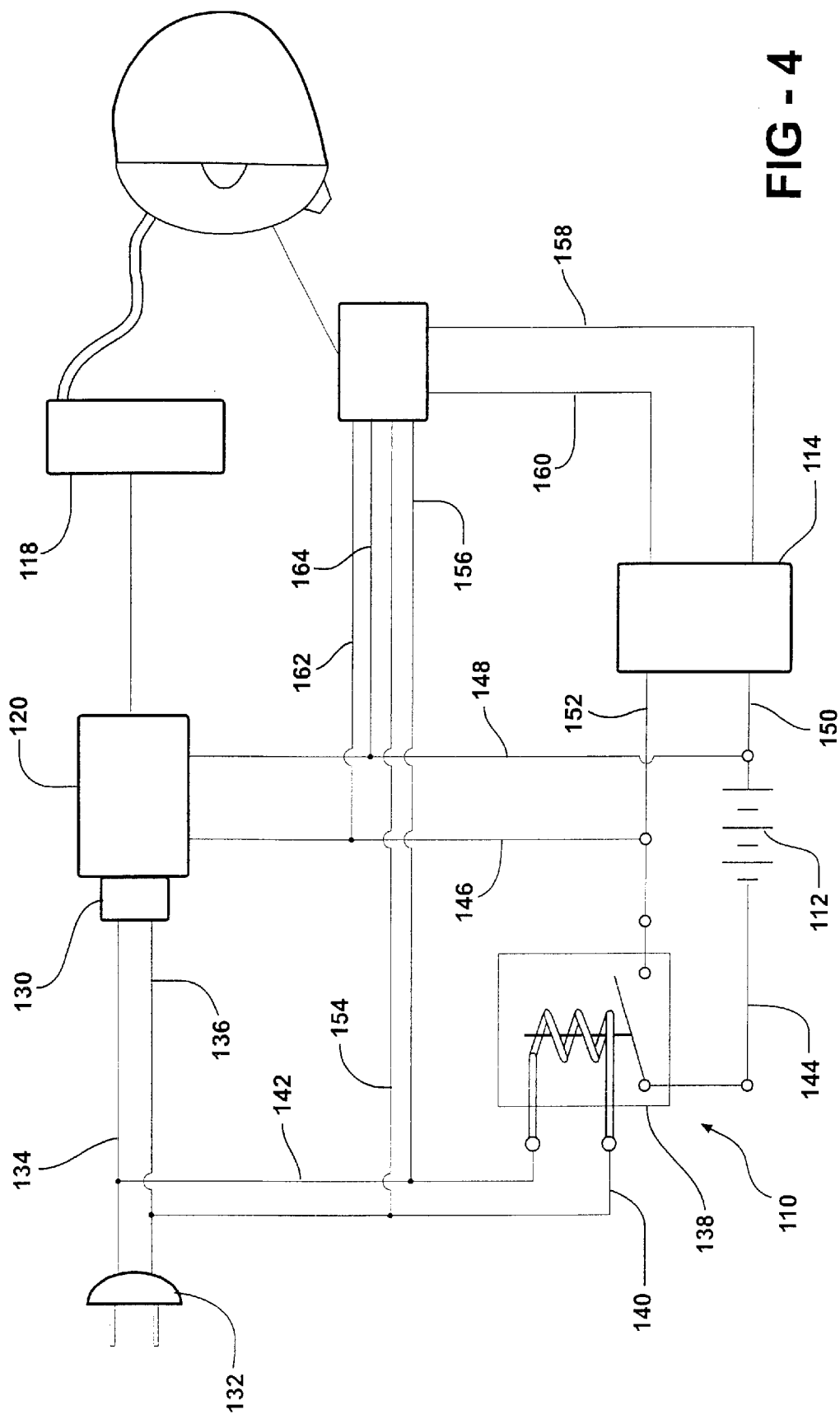
FIG. 4 is a circuit diagram of a continuous positive air pressure medical device control system including an alternating current interruption detector, an air pressure sensor, an audible alarm and an auxiliary direct current power source.

The continuous positive air pressure sleep apnea treatment device 110, shown in FIG. 4, has an auxiliary power source 112, an audible alarm 114 and an air pressure sensor 116. The pressure sensor 116 can, however, be any one of a variety of sensors usable in analysis or treatment devices. The device 110 includes a compressor 118 driven by a DC motor 120. The compressor 118 supplies compressed air to the mask 124 through a flexible tube 126. The mask 124 covers the nose of the wearer and is held in place by a strap 124. An air discharge 128 permits the discharge of air due to expiration by a person wearing the mask 124. The compressor 118 can also supply air under pressure to nose tubes rather than a mask 124.

The DC motor 120 has an AC to DC converter 130. The converter 130 is connected to an AC power source 132 by lines 134 and 136. An AC motor could be used in place of the DC motor 120 if desired. A DC to AC converter could then be used when supplying current to the AC motor from a battery. The compressor 118 could also be connected to an AC motor and a DC motor and driven by either the AC motor or the DC motor depending upon the power source available.

A relay 138 is connected to the AC power source 132 by lines 140 and 142. When current is supplied to the relay 138 from the AC power source 132, the contacts in the relay are held open. An interruption in current from the power source 132 will allow the contacts in the relay 138 to close. Closing the relay 138 connects one terminal of the battery to the motor 120 through the line 144, the relay and line 146. The other terminal of the battery 112 is connected to the motor 120 by a line 148. With this arrangement, if current to the power source 132 is interrupted, the battery 112 runs the motor 120. As soon as current from the AC power source 132 is restored, the relay 138 opens and the battery 112 is disconnected from the motor 120.

The audible alarm 114 is connected to one terminal of the battery 112 by a line 150. The alarm 114 is also connected to the line 146 by a line 152. With this arrangement the alarm 114 sounds any time there is an interruption in current from the power source 132. Some individuals with sleep apnea must be awakened if there is any interruption in the supply of compressed air to their mask 124. The system described above is intended to insure that the motor 120 receives current all the time and to provide an audible warning if there is any interruption in current from the power source 132.

A failure in the motor 120, the compressor 118 or the flexible tube 126 will result in a decrease in the pressure of air supplied to the mask 124. This decrease in pressure may reduce blood oxygen level and could be fatal for individuals with sleep apnea. Such a failure would not necessarily cause the relay 138 to close and activate the alarm 114. A pressure transducer 116 connected to the mask 124, the flexible tube 126 or the discharge of compressor 118 would permit detection of a failure other than a failure of the AC power source 132. The pressure transducer 116 may be connected to lines 140 and 142 by lines 154 and 156. Upon detection of an abnormal pressure, the pressure transducer 116 energizes the audible alarm 114 through lines 158 and 160. To operate the pressure transducer 116 when there is a failure in the power supply 132, the transducer is connected to the battery 112 through lines 162 and 164. The pressure transducer 116 could, if desired, be connected to. the line 144.and the lines 154 and 156 can be eliminated. With the lines 154 and 156 eliminated as suggested, the transducer 116 and audible alarm 114 are operated by the DC battery 112 only. Such an arrangement increases the load on the battery 112 and reduces the time between battery charges. However, with a system as shown in FIG. 4, the pressure transducer 116 and the audible alarm 114 would operate on AC as well as DC.

The medical equipment warning devices described above can be used with devices for the treatment of medical conditions other than sleep apnea. If a medicine in a gas or vapor form was to be supplied to the mask 36, 76 or 124, it could be added to the intake of the compressor 34, 74 or 118 or to the supply tube 38, 75 or 126 without changing the warning devices as described. The warning device shown in FIG. 1 can be used in combination with any electrical treatment or analytical device. A suitable container is provided for housing the warning device. The warning device of FIG. 1 can be housed in a small easy to transport case. The complete device shown in FIG. 4 may be packaged in multiple containers.

The disclosed embodiments are representative of presently preferred forms of the invention, but are intended to be illustrative rather than definitive thereof. The invention is defined in the claims.

I claim:

1. A medical equipment warning device comprising:

an AC energized relay, connectable to an AC power source for a medical treatment device, that is open when said AC power source is energized, that is closed when said AC power source is deenergized and that is automatically reopened upon restoration of said AC power source following an AC power source failure;

a DC circuit connected to the relay that is opened and closed by the relay;

a battery connected to the DC circuit;

an electric motor energized by the AC power source;

an air pump driven by the motor to supply air under pressure to a mask of a sleep apnea treatment device; and a signal generator in the DC circuit in series with the battery that produces a warning when the AC power source fails, the relay closes and the battery simultaneously energizes the signal generator.

2. A medical equipment warning device as set forth in claim 1 wherein the signed generator also produces a visual warning.

3. A medical equipment warning device as set forth in claim 1 wherein the physical warning is a vibration produced by a vibrator.

4. A medical equipment warning device as set forth in claim 1 including a DC motor in the DC circuit connected in parallel with the signal generator and a medical device driven by the DC motor.

5. A medical equipment warning device as set forth in claim 1 wherein the medical device driven by the DC motor is an air pump that supplies air under pressure to a mask of a sleep apnea treatment device.

6. A medical equipment warning device as set forth in claim 4 including an AC to DC converter connected to the DC motor and to the AC circuit for providing power to the DC motor when the AC power source is energized and the relay is open.

7. A medical equipment warning device as set forth in claim 1 including a manually operated switch in the DC circuit that is moved to an open position to deenergize the signal generator after a warning has been received from the signal generator.

8. A medical equipment warning device comprising:

an AC power source for a medical device;

an AC energized relay connected to the AC power source, for a medical device, that is open when the AC power source is energized, that is closed when the AC power source is deenergized and that is automatically reopened upon restoration of the AC power source following an AC power source failure;

a DC circuit connected to the relay;

a signal generator in the DC circuit;

a battery in the DC circuit;

a DC motor of a medical device in the DC circuit;

an AC to DC converter connected to the DC motor and to the AC power source; and wherein the signal generator is activated simultaneously with the closing of the AC energized relay.

* * * * *

UNITED STATES PATENT AND TRADEMARK OFFICE
CERTIFICATE OF CORRECTION

PATENT NO.       : 6,392,555 B1
APPLICATION NO. : 09/441609
DATED            : May 21, 2002
INVENTOR(S)      : Clark Most, Jr.

It is certified that error appears in the above-identified patent and that said Letters Patent is hereby corrected as shown below:

Section [56] References Cited, cancel 5,239,995 A 8/19 Estes et al, insert -- 5,535,738  7/16/96  Estes et al --.

Signed and Sealed this

Twenty-ninth Day of August, 2006

JON W. DUDAS
*Director of the United States Patent and Trademark Office*